United States Patent
Walsh et al.

(10) Patent No.: US 9,295,588 B2
(45) Date of Patent: Mar. 29, 2016

(54) METHOD AND APPARATUS FOR ATTACHING COMPONENTS TO ABSORBENT ARTICLES

(71) Applicant: The Procter & Gamble Company, Cincinnati, OH (US)

(72) Inventors: Bradley Edward Walsh, Cincinnati, OH (US); Paul Anthony Kawka, Guilford, IN (US); David Carlton Ordway, Oxford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 370 days.

(21) Appl. No.: 13/929,843

(22) Filed: Jun. 28, 2013

(65) Prior Publication Data

US 2014/0005021 A1 Jan. 2, 2014

Related U.S. Application Data

(60) Provisional application No. 61/665,928, filed on Jun. 29, 2012.

(51) Int. Cl.
*A61F 13/15* (2006.01)
*B29L 31/48* (2006.01)
(Continued)

(52) U.S. Cl.
CPC ............ *A61F 13/15* (2013.01); *A61F 13/15756* (2013.01); *B29C 65/48* (2013.01);
(Continued)

(58) Field of Classification Search
CPC ............ B29L 2031/4878; A61F 13/15; A61F 13/15756; B29C 66/8122; B29C 2793/0081; B29C 65/48; B29C 65/52; B29C 65/7847; B29C 65/7891; B29C 66/0042; B29C 66/1122; B29C 66/344; B29C 66/4722; B29C 66/7294; B29C 66/81423; B29C 66/81457; B29C 66/8225; B29C 66/8322; B29C 66/83411; B29C 66/9392; B29C 66/93441; B26D 5/20; B26D 1/205; B31B 1/90; B31B 1/72; B31B 1/94; B32B 38/185; B32B 31/1858; B32B 38/004; Y10T 156/1744; Y10T 156/1702; Y10T 156/1317
USPC .................. 156/354, 355, 446, 447, 521, 517
See application file for complete search history.

(56) References Cited

U.S. PATENT DOCUMENTS 3,848,594 A 11/1974 Buell
3,860,003 A 1/1975 Buell
(Continued)

FOREIGN PATENT DOCUMENTS

EP 0 565 606 B1 3/1995
EP 2 446 868 A1 5/2012
(Continued)

OTHER PUBLICATIONS

Written Opinion for WO2014005005.*
(Continued)

*Primary Examiner* — Sonya Mazumdar
(74) *Attorney, Agent, or Firm* — Sarah M. DeCristofaro; Abbey A. Lopez

(57) ABSTRACT

An apparatus for applying discrete components of a first substrate to a second substrate includes a programmable servo motor having a shaft. The servo motor is programmed to rotate the shaft in a first phase and a second phase at a variable angular velocity in a single direction. The apparatus also includes a crank member connected with the shaft, a connector link connected with the crank member, and a tamper member connected with the connector link. When the shaft rotates in the first phase, the tamper member travels from a first position to a second position to displace a selected portion of the second substrate into contact with the discrete component.

15 Claims, 13 Drawing Sheets

(51) Int. Cl.
*B29C 65/00* (2006.01)
*B32B 38/04* (2006.01)
*B26D 5/20* (2006.01)
*B62D 5/20* (2006.01)
*B29C 65/48* (2006.01)
*B29C 65/78* (2006.01)
*B32B 37/00* (2006.01)
*B32B 38/18* (2006.01)
*B32B 38/00* (2006.01)
*B29C 65/52* (2006.01)

(52) U.S. Cl.
CPC ......... *B29C65/7847* (2013.01); *B29C 65/7891* (2013.01); *B29C 66/0042* (2013.01); *B29C 66/1122* (2013.01); *B29C 66/344* (2013.01); *B29C 66/4722* (2013.01); *B29C 66/81423* (2013.01); *B29C 66/81457* (2013.01); *B29C 66/8225* (2013.01); *B29C 66/8322* (2013.01); *B29C 66/83411* (2013.01); *B29C 66/9392* (2013.01); *B29C 66/93441* (2013.01); *B29C 66/93451* (2013.01); *B62D 5/20* (2013.01); *B29C 65/52* (2013.01); *B29C 66/7294* (2013.01); *B29C 66/8122* (2013.01); *B29C 2793/0081* (2013.01); *B29L 2031/4878* (2013.01); *B32B 38/004* (2013.01); *B32B 38/1858* (2013.01); *Y10T 156/1317* (2015.01); *Y10T 156/1702* (2015.01); *Y10T 156/1744* (2015.01)

(56) References Cited

U.S. PATENT DOCUMENTS

| | | |
|---|---|---|
| 3,911,173 A | 10/1975 | Sprague, Jr. |
| 3,929,135 A | 12/1975 | Thompson |
| 4,324,246 A | 4/1982 | Mullane et al. |
| 4,342,314 A | 8/1982 | Radel et al. |
| 4,381,781 A | 5/1983 | Sciaraffa et al. |
| 4,463,045 A | 7/1984 | Ahr et al. |
| 4,573,986 A | 3/1986 | Minetola et al. |
| 4,609,518 A | 9/1986 | Curro et al. |
| 4,610,678 A | 9/1986 | Weisman et al. |
| 4,629,643 A | 12/1986 | Curro et al. |
| 4,662,875 A | 5/1987 | Hirotsu et al. |
| 4,673,402 A | 6/1987 | Weisman et al. |
| 4,695,278 A | 9/1987 | Lawson |
| 4,785,996 A | 11/1988 | Ziecker et al. |
| 4,795,454 A | 1/1989 | Dragoo |
| 4,808,178 A | 2/1989 | Aziz et al. |
| 4,834,735 A | 5/1989 | Alemany et al. |
| 4,842,666 A | 6/1989 | Werenicz |
| 4,846,815 A | 7/1989 | Scripps |
| 4,857,067 A | 8/1989 | Wood et al. |
| 4,888,231 A | 12/1989 | Angstadt |
| 4,894,060 A | 1/1990 | Nestegard |
| 4,909,803 A | 3/1990 | Aziz et al. |
| 4,925,520 A | 5/1990 | Beaudoin et al. |
| 4,946,527 A | 8/1990 | Battrell |
| 4,963,140 A | 10/1990 | Robertson et al. |
| 4,988,344 A | 1/1991 | Reising et al. |
| 4,988,345 A | 1/1991 | Reising |
| 5,006,394 A | 4/1991 | Baird |
| 5,137,537 A | 8/1992 | Herron et al. |
| 5,147,345 A | 9/1992 | Young et al. |
| 5,151,092 A | 9/1992 | Buell et al. |
| 5,221,274 A | 6/1993 | Buell et al. |
| 5,260,345 A | 11/1993 | Desmarais et al. |
| 5,342,338 A | 8/1994 | Roe |
| 5,387,207 A | 2/1995 | Dyer et al. |
| 5,518,801 A | 5/1996 | Chappell et al. |
| 5,562,646 A | 10/1996 | Goldman et al. |
| 5,571,096 A | 11/1996 | Dobrin et al. |
| 5,580,411 A | 12/1996 | Nease et al. |
| 5,595,567 A | 1/1997 | King et al. |
| 5,624,427 A | 4/1997 | Bergman et al. |
| 5,643,396 A | 7/1997 | Rajala et al. |
| 5,650,222 A | 7/1997 | Desmarais et al. |
| 5,669,894 A | 9/1997 | Goldman et al. |
| 5,674,216 A | 10/1997 | Buell et al. |
| 5,691,035 A | 11/1997 | Chappell et al. |
| 5,693,165 A | 12/1997 | Schmitz |
| 5,723,087 A | 3/1998 | Chappell et al. |
| 5,735,840 A | 4/1998 | Kline et al. |
| 5,865,823 A | 2/1999 | Curro |
| 5,916,663 A | 6/1999 | Chappell et al. |
| 5,928,212 A | 7/1999 | Kline et al. |
| 5,941,864 A | 8/1999 | Roe |
| 6,004,306 A | 12/1999 | Roe et al. |
| 6,010,491 A | 1/2000 | Roe et al. |
| 6,027,483 A | 2/2000 | Chappell et al. |
| 6,251,097 B1 | 6/2001 | Kline et al. |
| 6,414,215 B1 | 7/2002 | Roe |
| 6,432,098 B1 | 8/2002 | Kline et al. |
| 6,441,266 B1 | 8/2002 | Dyer et al. |
| 6,494,244 B2 | 12/2002 | Parrish et al. |
| 6,573,423 B1 | 6/2003 | Herrlein et al. |
| 6,596,108 B2 | 7/2003 | McCabe |
| 6,677,258 B2 | 1/2004 | Carroll et al. |
| 7,811,403 B2 | 10/2010 | Andrews |
| 8,377,249 B2 | 2/2013 | Gill |
| 2004/0162536 A1 | 8/2004 | Becker et al. |
| 2004/0167486 A1 | 8/2004 | Busam et al. |
| 2005/0215972 A1 | 9/2005 | Roe et al. |
| 2005/0215973 A1 | 9/2005 | Roe et al. |
| 2006/0189956 A1 | 8/2006 | Vatansever |
| 2007/0078427 A1 | 4/2007 | Raycheck et al. |
| 2007/0093769 A1 | 4/2007 | Kline et al. |
| 2007/0142798 A1 | 6/2007 | Goodlander et al. |
| 2007/0142806 A1 | 6/2007 | Roe et al. |
| 2007/0219521 A1 | 9/2007 | Hird et al. |
| 2007/0287348 A1 | 12/2007 | Autran et al. |
| 2007/0287982 A1 | 12/2007 | Lodge et al. |
| 2007/0287983 A1 | 12/2007 | Autran et al. |
| 2009/0294044 A1 | 12/2009 | Gill |
| 2010/0108268 A1 | 5/2010 | Yamamoto et al. |
| 2010/0252603 A1 | 10/2010 | Gill |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0139662 A1 | 6/2011 | Hird et al. |
| 2011/0152812 A1 | 6/2011 | Hird et al. |

FOREIGN PATENT DOCUMENTS

| | | |
|---|---|---|
| WO | WO 95/16746 | 6/1995 |
| WO | WO 00/02727 A1 | 1/2000 |
| WO | WO 2006/015141 | 2/2006 |
| WO | WO 2009/146307 A1 | 12/2009 |

OTHER PUBLICATIONS

PCT/International Search Report, dated Sep. 30, 2013, 11 pages.
U.S. Appl. No. 13/929,854, filed Jun. 28, 2013, Mark Mason Hargett.

* cited by examiner

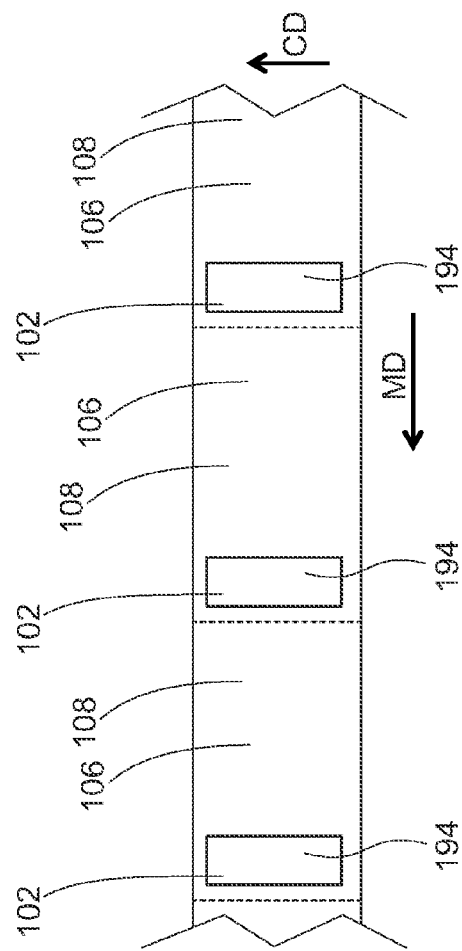
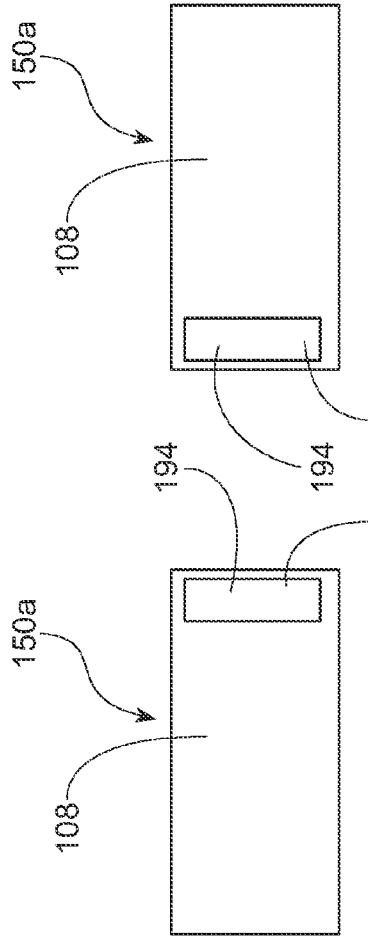
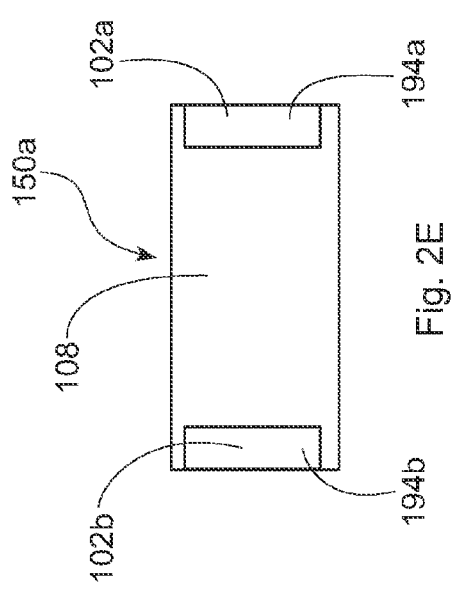
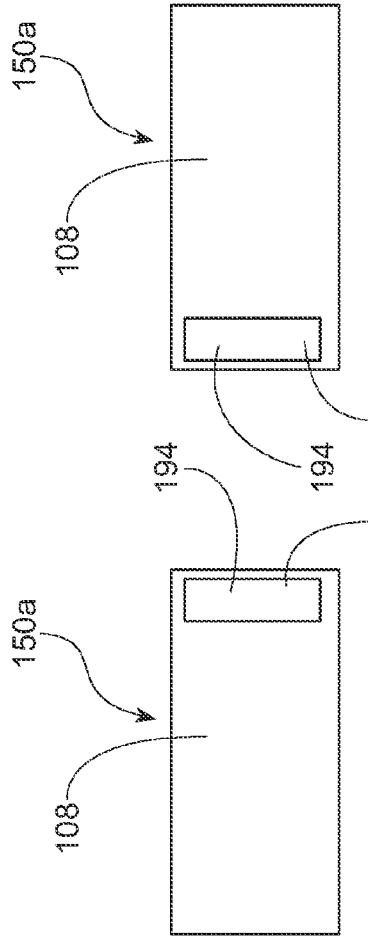

METHOD AND APPARATUS FOR ATTACHING COMPONENTS TO ABSORBENT ARTICLES

This application claims priority to U.S. Provisional Application Ser. No. 61/665,928, filed Jun. 29, 2012, which is hereby incorporated by reference in its entirety.

FIELD OF THE INVENTION

The present disclosure relates to methods and apparatuses for manufacturing disposable absorbent articles, and more particularly, methods and apparatuses for attaching components, such as waistbands, side panels, cuffs, or other components to disposable absorbent articles.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which, in turn, are then combined with other advancing webs of material. Webs of material and component parts used to manufacture diapers may include: back sheets, topsheet, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final cut to separate the web(s) into discrete diapers or other absorbent articles. The discrete diapers or absorbent articles may also then be folded and packaged.

Various methods and apparatuses may be used for attaching different components to the advancing web. Some of the methods and apparatuses relate to securing waistbands, and more particularly, elastic waistbands to an advancing web. In some processes, elastic waistbands are adhered to an advancing web in a stretched condition. However, some existing methods and apparatuses add cost and complexity to manufacturing processes. For example, the waistband material may be advanced in a first direction, stretched, rotated, and advanced in a second direction before being applied to an advancing web. In addition, in order to join waistbands advancing in the cross direction to a continuous web advancing in the machine direction, some processes may intermittently direct an advancing web toward the advancing waistband, which directs the advancing web away from the machine direction. As a result, the web may be mechanically strained to the point of rupture. In some processes, waistbands may be joined to the advancing web such that the waistbands are spaced apart along the machine direction of the advancing web. The spacing between adjacent waistbands may change from one size absorbent article to another size absorbent article. Such processes are not easily configurable to accommodate changes in the spacing and/or size of the waistbands. As a result, in order to change a process from producing one size absorbent article to producing a different size absorbent article, equipment may need to be altered or replaced, which in turn adds machine and labor costs to the process.

It may be desirable to provide a process for attaching components of absorbent articles advancing in a cross direction to a continuous web of absorbent articles advancing in a machine direction. It may be desirable to provide a process and apparatus for joining components of absorbent articles to advancing webs while minimizing the time the advancing web is directed away from the machine direction. It may also be desirable to provide a process and apparatus adaptable for joining components of absorbent articles of various sizes and spacing to an advancing web.

SUMMARY OF THE INVENTION

Aspects of the present disclosure involve an apparatus for applying discrete components, such as waistbands, cut from a first substrate to a second substrate. The apparatus may comprise a drum having an outer circumferential surface and a cutter positioned to cut the first substrate on the outer circumferential surface of the drum into a plurality of the discrete components. The apparatus may include a conveyor for positioning the second substrate proximate to, but not in contact with, the outer circumferential surface of the drum. The apparatus may also comprise a programmable servo motor having a shaft, wherein the shaft continuously rotates at a variable angular velocity in a single direction. The servo motor is configured to rotate the shaft in a first phase and a second phase. The shaft is constrained to rotate from a first angular position to a second angular position in a first time in the first phase and the shaft is thereafter constrained to rotate from the second angular position back to the first angular position in a second time in the second phase. The apparatus may also include a tamper member associated with the shaft of the servo motor. When the shaft rotates in the first phase, the tamper member travels from a first position to a second position to displace a selected portion of the second substrate into contact with the discrete component on the outer circumferential surface of the drum.

Aspects of the present disclosure may involve an apparatus for applying discrete components of a first substrate to a target area of a second substrate. The apparatus may comprise a programmable servo motor having a shaft, wherein the shaft continuously rotates at a variable angular velocity in a single direction. The servo motor is programmed to rotate the shaft in a first phase and a second phase. The shaft is constrained to rotate from a first angular position to a second angular position in a first time in the first phase and the shaft is constrained to rotate from the second angular position to the first angular position in a second time in the second phase. The apparatus may include a crank member connected with the shaft and a connector link connected with the crank member. The apparatus includes a tamper member connected with the connector link. The tamper member is positioned proximate to the second substrate in line with a discrete component of the first substrate. The second substrate may comprise a target area. When the shaft rotates in the first phase, the tamper member travels from a first position to a second position to displace the target area of the second substrate into contact with the discrete component.

Aspects of the present disclosure also include a method for applying discrete components of a first substrate to a second substrate, the method comprising the steps of: rotating a drum about an axis of rotation, the drum having an outer circumferential surface; advancing the first substrate onto the outer circumferential surface of the drum; advancing the second substrate proximate to the outer circumferential surface of the drum, the second substrate having a first surface and a second surface, wherein the second surface comprises a target area; cutting the first substrate into discrete components on the outer circumferential surface of the drum, the discrete components having a first surface and an opposing second surface; continuously rotating a shaft of a motor at a variable angular velocity in a single direction, wherein the motor is configured to rotate the shaft in a first phase and a second phase, wherein the shaft is constrained to rotate from a first angular position to a second angular position in a first time in the first phase, wherein the shaft is constrained to rotate from the second angular position to the first angular position in a second time in the second phase; shifting a tamper member from a first position to a second position toward the second substrate and the outer circumferential surface of the drum as the shaft of the motor rotates in the first phase; displacing the second substrate such that the target area of the second substrate contacts the first surface of a discrete component on the drum; and shifting the tamper member from the second position back to the first position as the shaft of the motor rotates in the second phase.

BRIEF DESCRIPTION OF THE DRAWINGS

FIG. 2D is a plan view of a continuous length of absorbent articles having discrete waistbands.

FIG. 2E is a plan view of an exemplary absorbent article having two discrete waistbands.

FIG. 2F is a plan view of an exemplary absorbent article having one discrete waistband.

FIG. 2G is a plan view of an exemplary absorbent article having one discrete waistband.

DETAILED DESCRIPTION OF THE INVENTION

Figure 1:
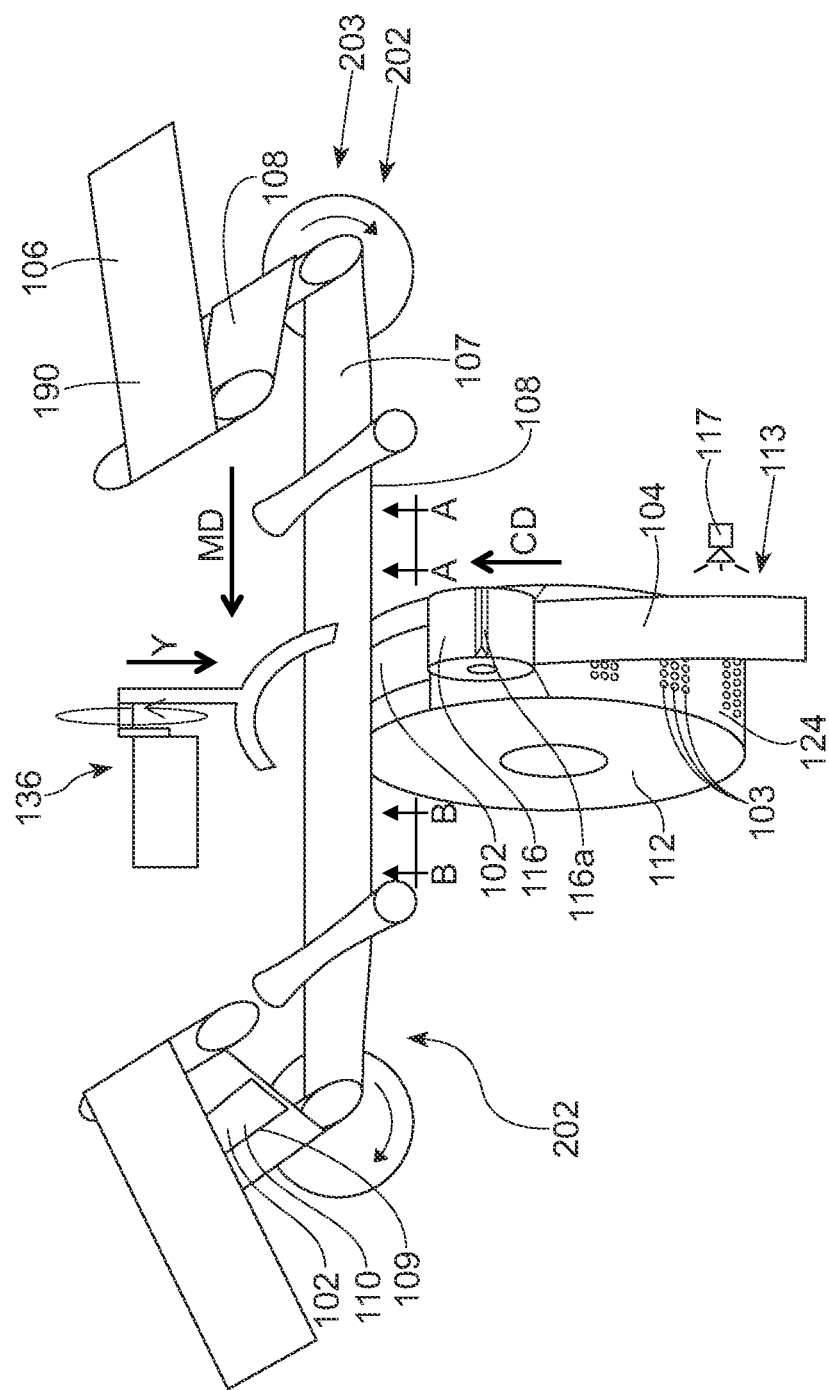
FIG. 1 is a perspective view of an apparatus for joining discrete components to a continuous length of absorbent articles.

The following term definitions may be useful in understanding the present disclosure:

"Absorbent article" is used herein to refer to consumer products whose primary function is to absorb and retain soils and wastes.

"Diaper" is used herein to refer to an absorbent article generally worn by infants and incontinent persons about the lower torso.

"Disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

"Disposed" is used herein to mean that an element(s) is formed (joined and positioned) in a particular place or position as a macro-unitary structure with other elements or as a separate element joined to another element.

As used herein, "joined" encompasses configurations whereby an element is directly secured to another element by affixing the element directly to the other element, and configurations whereby an element is indirectly secured to another element by affixing the element to intermediate member(s) which in turn are affixed to the other element.

"Substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a layer or layers or fibrous materials, films and foils such as plastic films or metallic foils that may be used alone or laminated to one or more web, layer, film and/or foil. As such, a web is a substrate.

"Nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern.

"Machine direction" (MD) is used herein to refer to the direction of a second substrate through a process.

"Cross direction" (CD) is used herein to refer to a direction that is generally not parallel to, and usually perpendicular to, the machine direction in the XY plane of the material.

"Elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. The term "inelastic" refers herein to any material that does not fall within the definition of "elastic" above.

"Stretchable" refers to materials that are capable of extending in at least one direction to a certain degree without undue rupture.

The present disclosure relates to methods and apparatuses for joining substrates. As discussed in more detail below, the process may be utilized in an absorbent article assembly configuration wherein discrete components, such as waistbands, are held on an outer surface of a rotating drum. A tamper apparatus may include a tamper member that directs a target area of an advancing substrate into contact with the discrete components on the drum. Adhesive may be applied to the discrete components and/or substrate to adhere the substrate and the discrete components together. The tamper member may be operatively connected with the shaft of a servo motor. In some configurations, a crank member may be connected with the motor shaft and connected with a connector link. The connector link operatively connects the tamper member with the crank member. The motor shaft may be configured to continuously rotate at a variable angular velocity in a single direction. In some instances, the servo motor is configured to rotate the motor shaft in a first phase and a second phase, wherein the motor shaft is constrained to rotate from a first angular position to a second angular position in a first time in the first phase. In addition, the shaft may be constrained to rotate from the second angular position to the first angular position in a second time in the second phase. When the shaft rotates in the first phase, the tamper member travels from a first position to a second position to displace a selected portion of the substrate into contact with a discrete component on the drum. When the shaft rotates in the second phase, the tamper member travels from the second position to the first position to move away from the substrate.

As discussed below, the tamper apparatus may include various links and/or tracks to define the travel path of the reciprocating movement of the tamper member. For example, some configurations may include guide links that pivotally connect the tamper member to a base. The tamper apparatus may include a compressible member disposed along a bottom surface of the tamper member. In some configurations, the tamper member may be slidingly connected with guide bars that define a straight line reciprocating travel path.

In some joining operations, a drum is rotated about an axis of rotation and a first substrate advances onto an outer circumferential surface of the drum. A conveyor concurrently advances a second substrate in a machine direction adjacent to the drum. The drum may be oriented such that the first substrate is advanced in a cross direction with respect to the second substrate. The tamper apparatus is positioned adjacent the second substrate such that the second substrate is between the tamper apparatus and the outer circumferential surface of the drum. Adhesive may be applied to the first substrate prior to or while the first substrate is advancing on the drum. While advancing on the outer circumferential surface of the drum, the first substrate may be cut into discrete components. As the drum rotates to position the discrete components adjacent the second substrate on the drum, the servo motor drives the tamper member toward the outer circumferential surface of the drum. The tamper member directs the second substrate into contact with the discrete component on the outer circumferential surface of the drum. Adhesive on the discrete component attaches the discrete components to the second substrate. The servo motor then drives the tamper member away from the outer circumferential surface of the drum and the second substrate continues advancing in the machine direction with the discrete component attached. The process is repeated to join each discrete component to the second substrate. As such, the discrete components are spaced apart from each other discrete component on the second substrate in the machine direction.

The servo motor is configured to rapidly drive the tamper member toward and away from the outer circumferential surface of the drum in order to minimize the contact time between the tamper member and the advancing second substrate. As such, the motor angular velocity is greatest when the tamper member is relatively near to the outer circumferential surface of the drum. The angular velocity of the motor increases in the first phase as the tamper member moves toward the drum and decreases in the second phase as the tamper member moves away from the drum. By operating the motor at variable angular velocities, the motor can be configured to slow down when the tamper member is away from the outer circumferential surface of the drum to allow a subsequent discrete component time to advance adjacent the second substrate and the drum. Furthermore, the servo motor can be re-programmed to account for changes in the desired outputs without the need to change or alter existing equipment. Additionally, the mechanism connected to the servo motor is relatively smaller in size compared to a mechanical cam mechanism.

It is to be appreciated that although the methods and apparatuses herein may be configured to join various types of substrates and discrete components, the methods and apparatuses herein are discussed below in the context of manufacturing absorbent articles. In particular, the methods and apparatuses are discussed in the context of joining discrete elastic components to a continuous length of absorbent articles. While the present disclosure relates mainly to addition of elastic components such as waistbands to diapers, it is to be appreciated that the methods and apparatuses disclosed herein can also be applied to other discrete components used on diapers as well as other types of absorbent articles. For example, elastic components can include pre-stretched ears or side panels, cuffs placed in a side saddle process where the product's waist regions are parallel to the machine direction, or other components requiring stretch in the cross direction. In other applications, the discrete elastic components can comprise elastic topsheets for a diaper cut from a substrate stretched in the cross direction before being connected with other diaper components, such as a backsheet. In addition, other applications may include the addition of various inelastic components such as backsheets, topsheet, absorbent cores, front and/or back ears, and fastener components.

It is to be appreciated that the first substrate may be constructed from various types of materials. For example, the first substrate may include a combination of layered elastic substrates such as elastic films, poly films, and nonwovens. In some examples, the first substrate may be constructed from a single elastic or poly film. In yet other examples, the first substrate may be constructed from a single layer nonwoven. It should also be appreciated that second substrate may include various components of an assembled absorbent article, such as, for example, a topsheet and/or a backsheet. Various types of suitable materials for various diaper components are discussed in more detail below with reference to an example diaper embodiment.

As previously mentioned, the apparatuses and methods disclosed herein may be configured to join waistbands to a continuous length of absorbent articles as the absorbent articles are being manufactured. For example, as shown in FIG. 1, a first substrate 104 may continuously advance onto an outer circumferential surface 124 of a rotating drum 112 in a stretched state. Concurrently, a second substrate 106 may advance in a machine direction MD adjacent the outer circumferential surface 124 of the drum 112. The drum 112 may be oriented such that the first substrate is advanced in a cross direction CD with respect to the machine direction of the second substrate 106. Adhesive 113 may be applied by adhesive applicator 117 to the first substrate 104 before the first substrate 104 advances onto the drum 112. The drum 112 may rotate at a velocity such that the outer circumferential surface 124 of the drum 112 travels at the same speed as the first substrate 104. The drum 112 may be configured with vacuum openings 103 for applying vacuum force to hold the first substrate 104 on the outer circumferential surface 124, while maintaining cross directional stretch in the first substrate 104. While the first substrate 104 is advancing on the drum 112, a cutter 116, shown in the form of a rotating knife roll 116a for purposes of illustration, may cut the first substrate 104 into discrete components 102. Vacuum force may be used to maintain stretch in the discrete components 102 after being cut. While it is shown that the first substrate 104 is cut by a rotating knife roll 116a, it is to be appreciated that various other cutters may be used.

With continued reference to FIG. 1, the discrete components 102 are individually transferred from the drum 112 to the second substrate 106 with a tamper apparatus 136. A conveyor 202 may advance the second substrate 106 in the machine direction MD. The conveyor 202 may be configured to periodically slow or stop the movement of the second substrate 106 in the machine direction MD. For example, the conveyor 202 may include a localized speed varying apparatus 203, such as shown in FIG. 1. It is to be appreciated that various types of localized speed varying apparatuses may be used. Exemplary localized speed varying apparatuses may include those described in U.S. Pat. No. 5,693,165 issued to Schmitz on Dec. 2, 1997; U.S. Pat. No. 6,596,108 issued to Mccabe on Jul. 22, 2003; and U.S. Patent Publication No. 2010/0252603 published on Oct. 7, 2010. As the second substrate 106 is stopped, the tamper apparatus 136 moves the second substrate 106 into contact with a discrete component 102, subsequently removing the discrete component 102 from the outer circumferential surface 124 of the drum 112 and attaching the discrete component 102 to the second substrate 106 with adhesive 113. Vacuum may be intermittently interrupted in order to assist removal of the discrete component 102 from the outer circumferential surface 124 of the drum 112. The tamper apparatus 136 then moves away from the second substrate 106, while the second substrate 106 and the discrete component 102 continue advancing in the machine direction MD. The attachment process is repeated to join each discrete component 102 to the second substrate 106. Exemplary processes for attaching elastic components to absorbent articles are described in U.S. Provisional Patent Application No. 61/665,930.

Figure 2A:
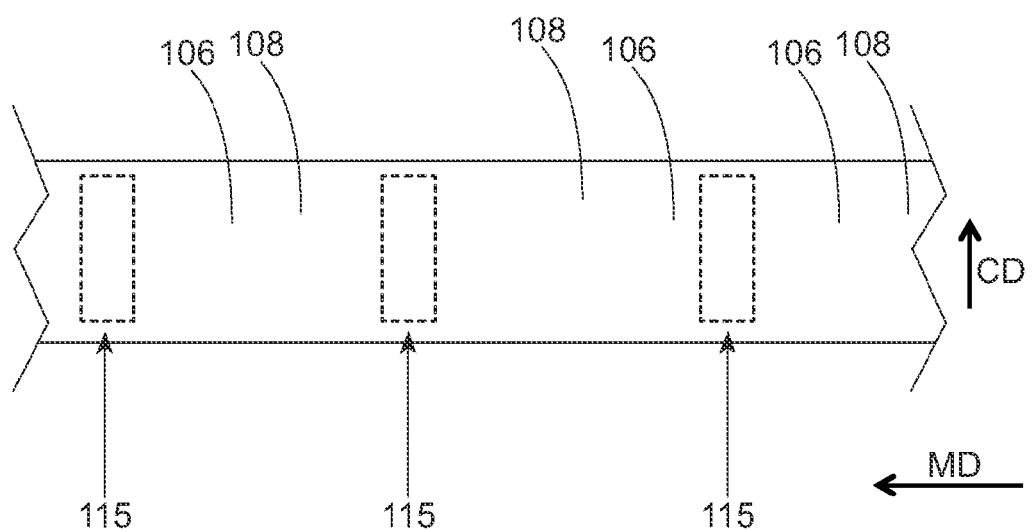
FIG. 2A is a plan view of a continuous length of absorbent articles from FIG. 1 taken along line A-A before discrete waistbands are affixed by the apparatus.
Figure 2B:
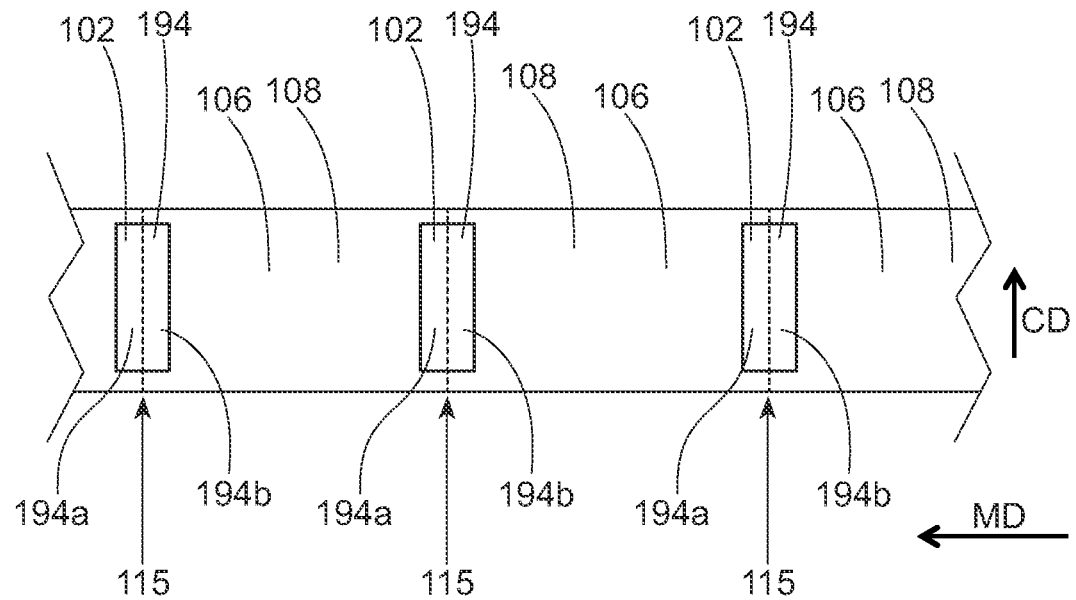
FIG. 2B is a plan view of a continuous length of absorbent articles from FIG. 1 taken along line B-B after discrete waistbands are affixed by the apparatus.
Figure 2C:
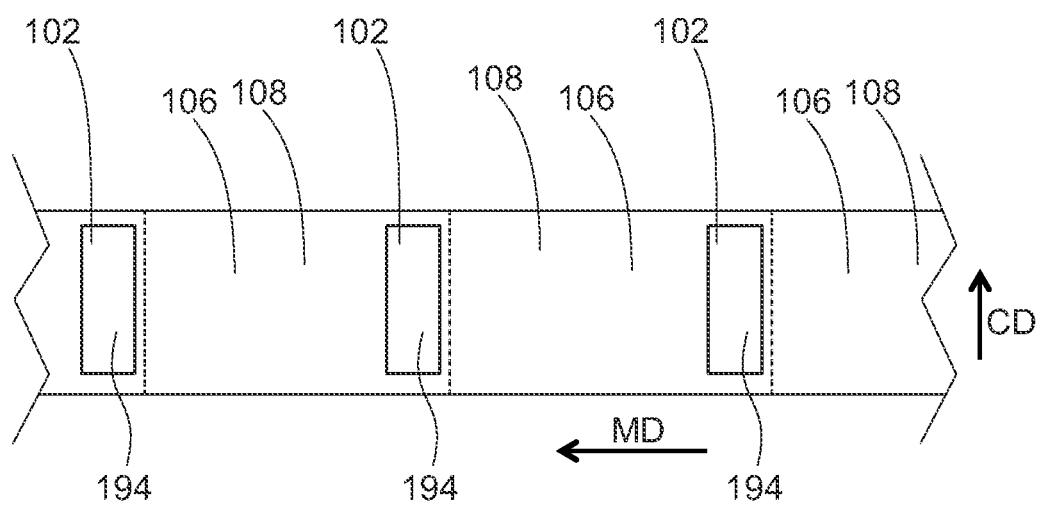
FIG. 2C is a plan view of a continuous length of absorbent articles having discrete waistbands.

FIG. 2A shows the continuous length of second substrate 106 before attaching the discrete components. As shown in FIG. 2A, the second substrate 106 may have a plurality of target areas 115 positioned where the discrete components are to be attached to the second substrate 106. As shown in FIG. 2B, the discrete components 102, shown as discrete waistbands 194 for purposes of illustration, may be joined at each target areas 115. Once the discrete waistbands 194 are joined, the second substrate 106, and thus the discrete waistband 194, may be cut in the cross direction CD to create a first waistband 194a on an absorbent article 104 and a second waistband 194b on a subsequently advancing absorbent article 104. In some exemplary configurations, as shown in FIGS. 2C and 2D, the second substrate 106 may be cut adjacent to the discrete waistband 194, either before or after the discrete waistband 194, thereby creating an absorbent article 150a having only one discrete waistband 194. In some exemplary configurations, absorbent articles 150a may have one discrete waistband 194 as shown in FIGS. 2F and 2G, or may have two discrete waistbands 194a and 194b as shown in FIG. 2E. It is to be appreciated that the absorbent articles 150a may have discrete waistbands arranged in various configurations. As discussed below, the method steps disclosed herein can be carried out in different ways by various types of mechanisms.

Figure 3A:
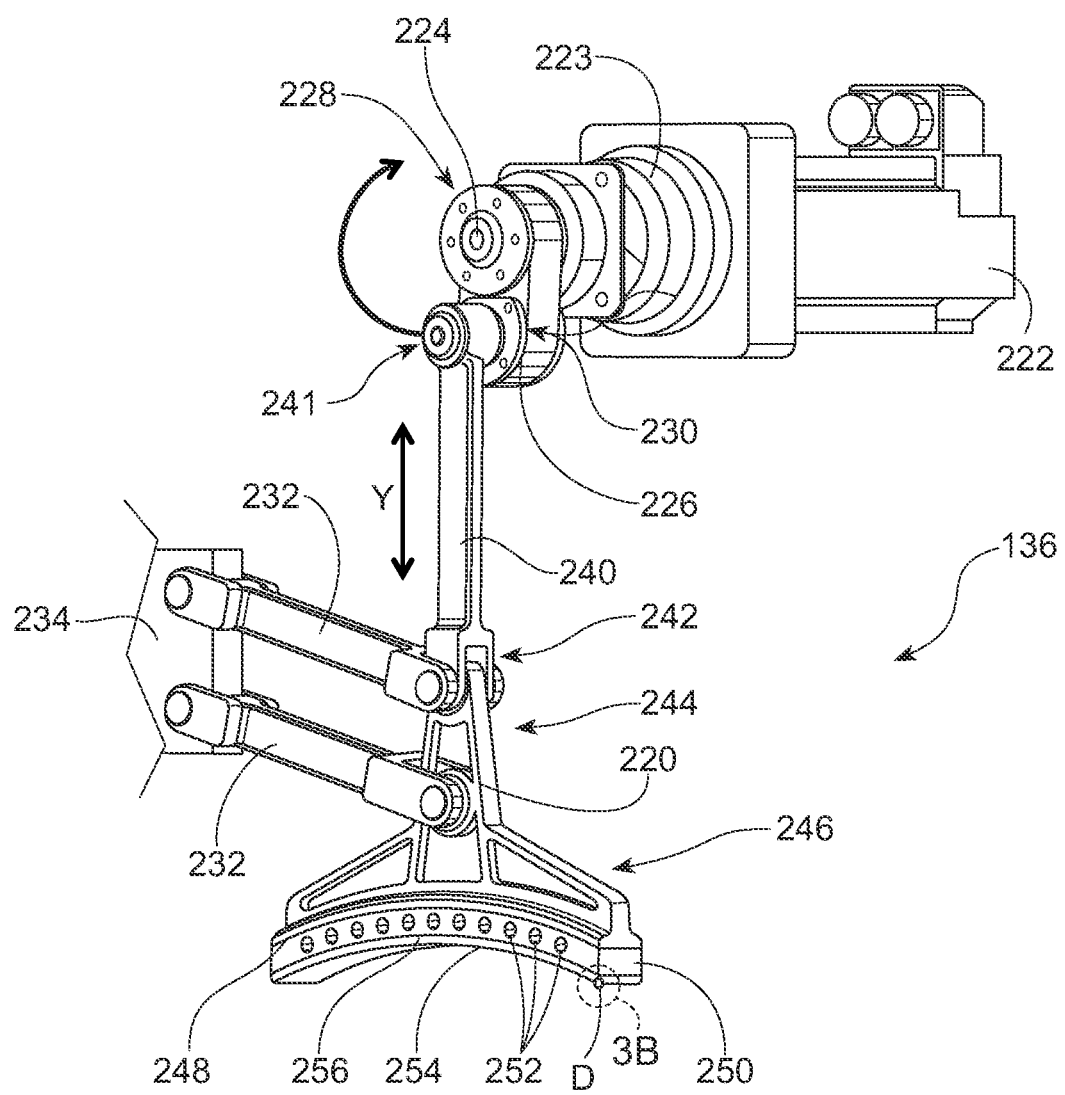
FIG. 3A is a perspective view of a tamper apparatus.

FIG. 3A shows a detailed perspective view of an embodiment of a tamper apparatus 136 that may be used to join discrete components to a substrate. As shown in FIG. 3A, the tamper apparatus 136 may include a tamper member 220 operatively connected to a motor 222 at a shaft 224 of the motor 222. The tamper apparatus 136 may also include a crank member 226 that is rotatably connected to the shaft 224 of the motor 222 in a first portion 228 of the crank member 226 and operatively connected to a connector link 240 in a second portion 230. The connector link 240 operatively connects the tamper member 220 to the crank member 226. The tamper apparatus 136 may also include a set of guide links 232 that pivotally connect the tamper member 220 to a base 234. The tamper apparatus 136 may include a compressible member 250 operatively connected to a bottom surface 248 of the tamper member 220.

Figure 3B:
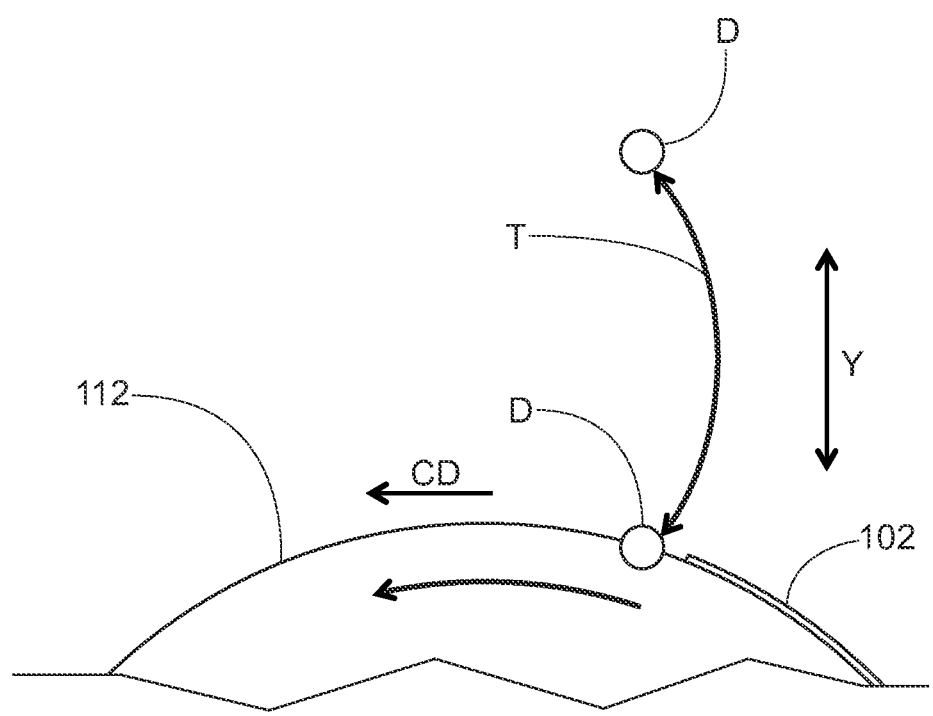
FIG. 3B is an elevation view of a point D on the tamper apparatus of FIG. 3A showing the reciprocating movement of the tamper member in the vertical direction in a defined trajectory.

With reference to FIGS. 1 and 3A, during operation, the motor 222 is configured to continuously rotate the shaft 224 of the motor 222 at a variable angular velocity in a single direction. A second substrate 106 may advance in the machine direction MD by a conveyor 202, while the discrete components 102 advance in the cross direction CD on a rotating drum 112, such that the second substrate 106 is positioned between the tamper apparatus 136 and the discrete component 102 on the outer circumferential surface 124 of the drum 112. As the shaft 224 rotates, the crank member 226 rotates in the same direction as the shaft 224 of the motor 222. Subsequently, the connector link 240 and the guide links 232 pivot, causing the tamper member 220 to move in the vertical direction, Y. The shaft 224 may continuously rotate in a single direction, causing the tamper member 220 to reciprocate toward and away from the drum 112 in the vertical direction, Y. FIG. 3B shows a point D of the tamper apparatus 136 from FIG. 3A reciprocating in the vertical direction, Y, in a defined trajectory, T. Following the vertical positioning of point D demonstrates the reciprocating movement of the tamper apparatus 136 as it moves toward and away from the drum 112.

Figure 4A:
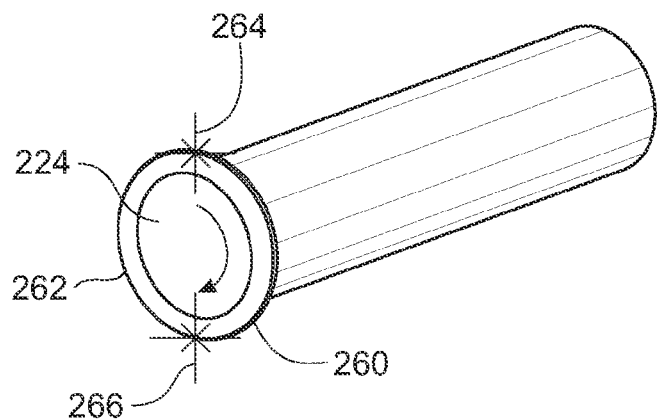
FIG. 4A is a schematic, perspective view showing a shaft of a motor rotating from a first angular position to a second angular position, and back to a first angular position.
Figure 4B:
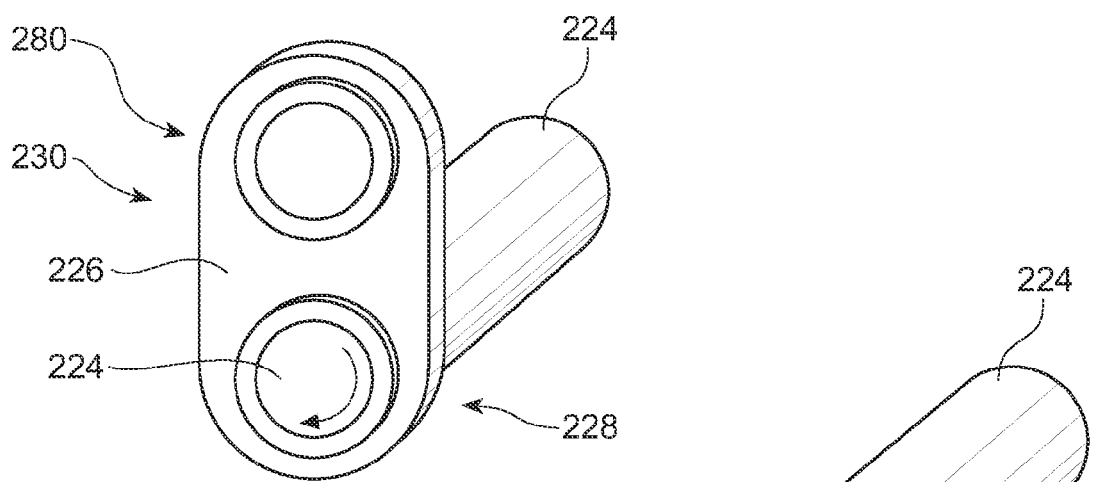
FIG. 4B is schematic, perspective view of a shaft of a motor in a first angular position connected with a crank member in a first position.
Figure 4C:
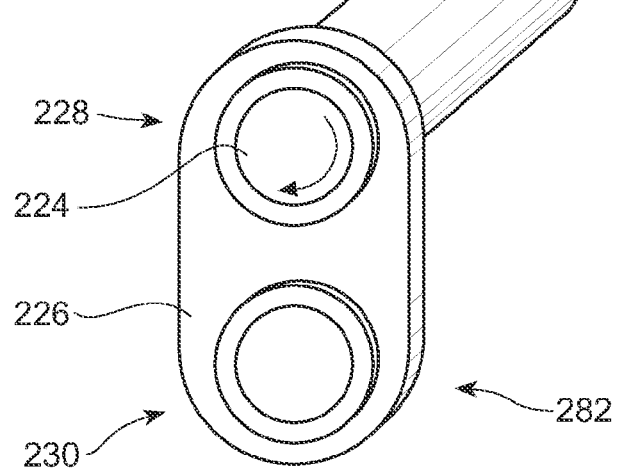
FIG. 4C is a schematic, perspective view of a shaft of a motor in a second angular position connected with a crank member in a second position.

FIG. 4A shows a schematic view of a motor shaft rotating from a first angular position to a second angular position, and back to a first angular position. With reference to FIGS. 3A, 4A, 4B, and 4C, the motor 222 is configured to rotate the shaft 224 in a first phase 260 and a second phase 262. In the first phase 260, the shaft 224 of the motor 222 rotates from a first angular position 264 to a second angular position 266 in a first time, causing the crank member 226 to rotate from a first position 280 shown in FIG. 4B to a second position 282 shown in FIG. 4C. In the second phase 262, the shaft 224 of the motor 222 rotates from a second angular position 266 back to the first angular position 264 in a second time, causing the crank member 226 to concurrently rotate from a second position 282 to a first position 280. As discussed in more detail below, as the crank member 226 rotates from a first position 280 to a second position 282, the tamper member 220 shifts toward the drum from a first position to a second position. Subsequently, the crank member 226 rotates from a second position 282 to a first position 280 and the tamper member 220 shifts away from the drum.

A motor 222 may be used to drive the tamper apparatus 136 such as shown in FIG. 3A. In particular, the motor 222 may, for example, be a programmable servo motor. For high speed manufacturing processes, such as in the production of absorbent articles, the variable angular velocity and requisite accelerations may require a motor with low inertia and high torque to inertia properties. As shown in FIG. 3A, the servo motor 222 includes a gear box 223 to provide speed and torque conversions to the tamper apparatus 136. An exemplary programmable servo motor 222 is manufactured by Rockwell Automation, Inc. of Milwaukee, Wisconsin, under the designation MPL-B330P. It is to be appreciated that one of ordinary skill in the art could program the servo motor if provided with the desired tamper member outputs.

With continuing reference to FIG. 3A, the tamper apparatus 136 may also include a crank member 226. The crank member 226 may be defined by a first portion 228 and a second portion 230. The first portion 228 of the crank member 226 may be operatively connected to the shaft 224 of the motor 222 such that the crank member 226 rotates with the shaft 224 of the motor 222 in the same direction. The second portion 230 of the crank member 226 may be rotatably connected to a first end 241 of the connector link 240. In some exemplary configurations, bearings may be used to connect the second portion 230 of the crank 226 to the first end 241 of the connector link 240.

The tamper apparatus 136 may also include a tamper member 220 as shown in FIG. 3A. The tamper member 220 may have a first portion 244 and a second portion 246. The second portion 246 of the tamper member 220 may define a bottom surface 248. The first portion 244 of the tamper member 220 may be operatively connected to a second end 242 of the connector link 240. The second portion 246 of the tamper member 220 may be substantially perpendicular to the first portion 244 of the tamper member 220, forming a substantially T-shaped member. The bottom surface 148 of the tamper member 220 may be contoured to match the contour of the outer circumferential surface of the drum. The bottom surface 248 of the tamper member 220 may be larger than a discrete component such that the tamper member 220 may press the second substrate against the entire discrete component. It is to be appreciated that a tamper member 220 configured for one size discrete component may be used to attach discrete components of various sizes. In some exemplary configurations, the tamper member 220 may be made from a light-weight metal material such as, for example, aluminum or titanium.

With reference to FIG. 3A, the tamper apparatus 136 may also include a compressible member 250 disposed along the bottom surface 248 of the tamper member 220. The compressible member 250 may be made of a material such as, for example, foam or rubber that compresses upon application of pressure to the compressible member. In some exemplary configurations, the compressible member 250 may have void spaces 252 such as shown in FIG. 3A. The compressible member may have an arcuate shape to match the contour of the outer circumferential surface of the drum. It is to be appreciated that a bottom surface 254 of the compressible member 250 may include a skin 256 to prevent the tamper apparatus 136 from sticking to the second substrate. The skin 256 may be made of a non-stick material such as urethane for example.

The tamper apparatus 136 may also include guide links 232 as shown in FIG. 3A. One end of each guide link may be operatively connected to the first portion 244 of the tamper member 220. The other end of each guide link 232 may be operatively connected to a base 234. While FIG. 3A shows two guide links 232, it is to be appreciated that fewer or greater than two guide links 232 may be used.

In operation, a continuous length of second substrate is advanced in the machine direction MD and discrete components are advanced in the cross-direction CD proximate to the tamper apparatus as shown in FIG. 1. The second substrate 106 advances in the machine direction MD proximate to the tamper apparatus 136 by a conveyor 202. The second substrate 106 may be defined by a first surface 107 and a second surface 108. At the same time as the second substrate 106 advances in the machine direction MD, discrete components 102 advance on the outer circumferential surface 124 of the rotating drum 112 in the cross direction CD such that the second substrate 106 is between the tamper apparatus 136 and the discrete components 102 on the outer circumferential surface 124 of the drum 112. The discrete components 102 may be defined by a first surface 109 and a second surface 110. As discussed in more detail below, the tamper apparatus 136 is configured to reciprocate from a first configuration to a second configuration and back to a first configuration to join the first surface 109 of the discrete components 102 to the second surface 108 of the second substrate 106.

Figure 5:
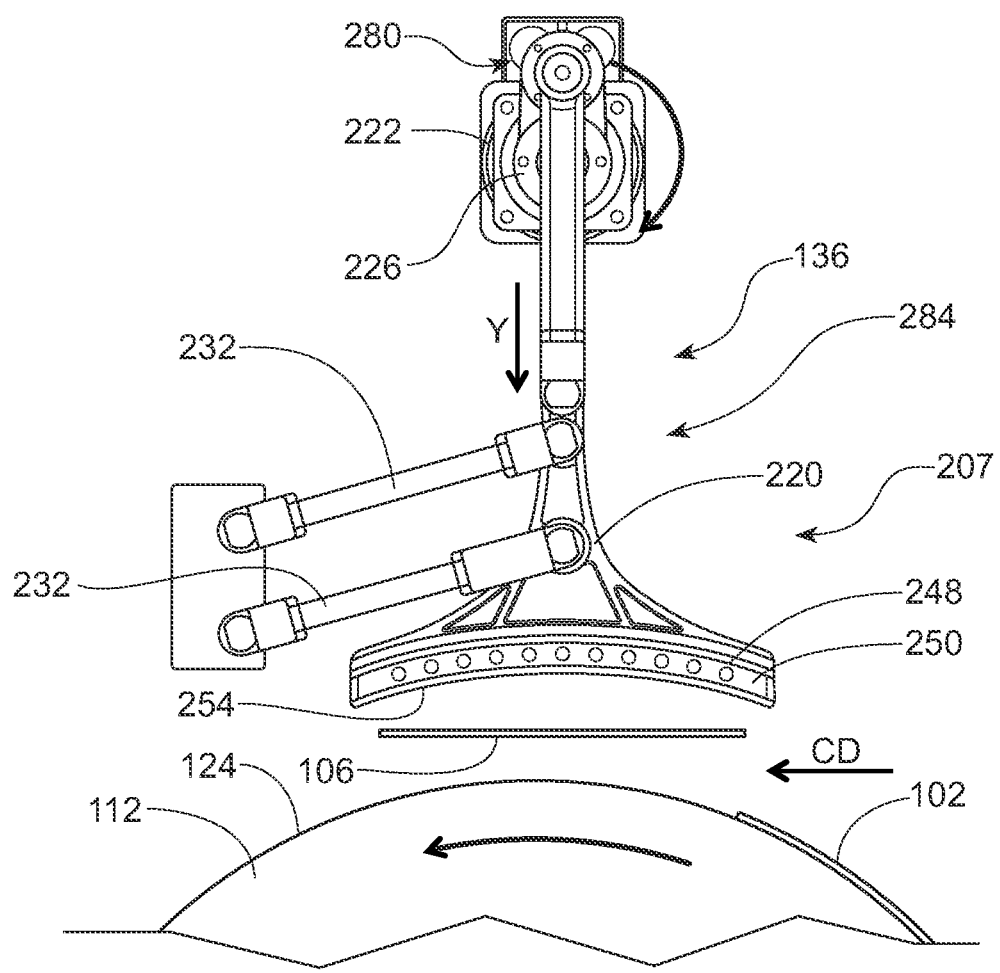
FIG. 5 is an elevation view of a tamper apparatus in a first configuration.
Figure 6:
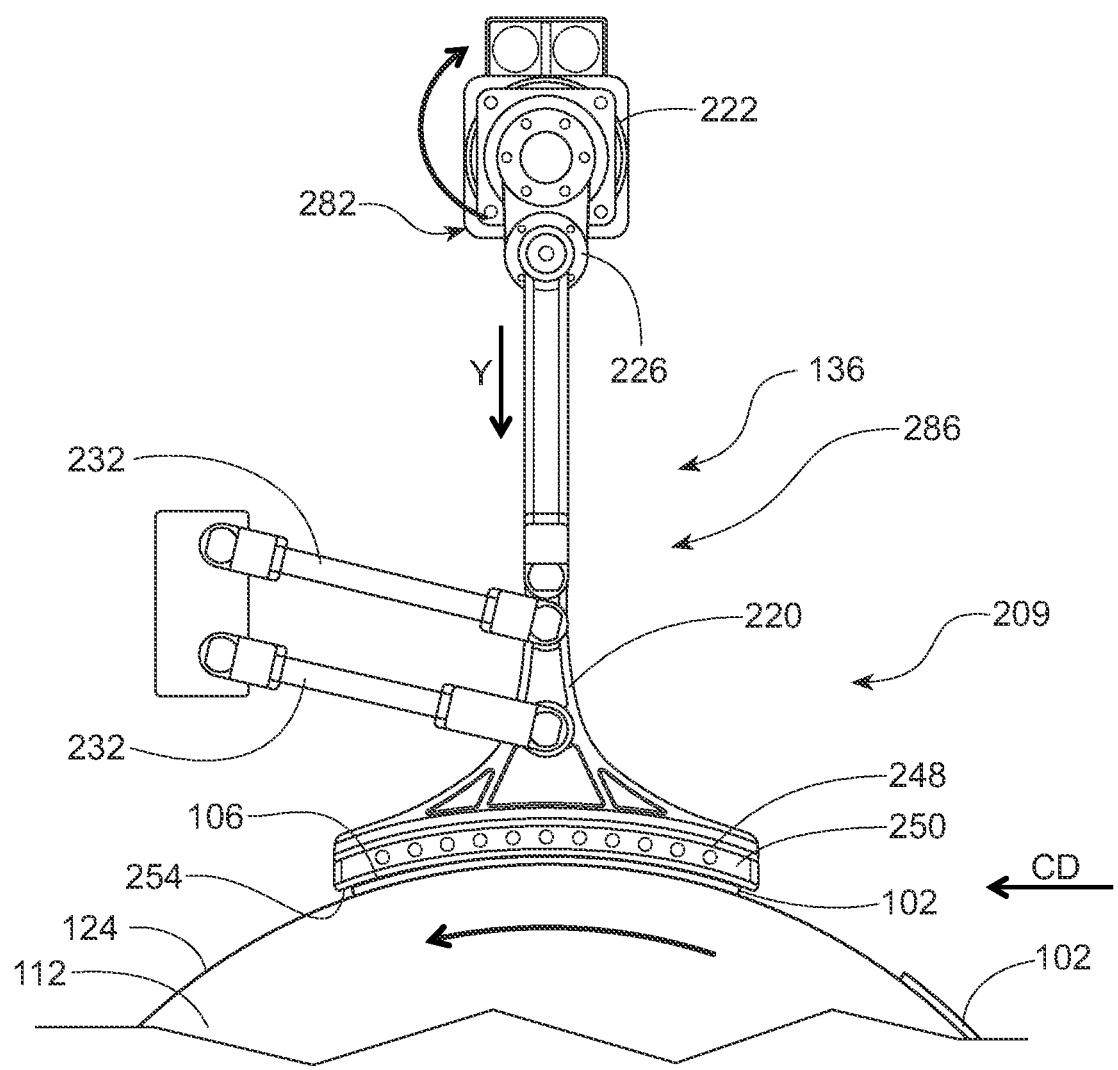
FIG. 6 is an elevation view of a tamper apparatus in a second configuration.

FIG. 5 shows a front elevation view of a tamper apparatus 136 in a first configuration 284. In a first configuration 284, the crank member 226 is in a first position 280 and the tamper member 220 is in a first position 207, positioned away from the second substrate 106 and the outer circumferential surface 124 of the drum 112. FIG. 6 shows a front elevation view of a tamper apparatus 136 in a second configuration 286. In a second configuration 286, the crank member 226 is in a second position 282 and the tamper member 220 is in a second position 209, pressing the second substrate 106 against the discrete band 102 on the outer circumferential surface 124 of the drum 112.

As shown in FIGS. 5 and 6, the contour of the bottom surface 248 of the tamper member 220 may match the contour of the outer circumferential surface 124 of the drum 112 such that the second substrate 106 uniformly presses the discrete components 102 between the tamper member 220 and the outer circumferential surface 124 of the drum 112. It is to be appreciated the discrete components may advance by a conveyor or a variety of other apparatuses having a contours different than that of the outer circumferential surface of the drum.

Referring to FIGS. 1, 3A-6, the servo motor 222 continuously rotates the shaft 224 of the motor 222 at a variable angular velocity in a single direction. In one revolution, the tamper apparatus 136 starts in a first configuration 284. In the first configuration 284, the shaft 224 of the motor 222 starts at a first angular position 264 and the crank member 226 also starts in first position 280. As the shaft 224 of the motor 222 rotates, the crank member 226 rotates in the same direction. The second portion 230 of the crank member 226 rotates in a circular path around the shaft 224 of the motor 222. At the same time, the bearings that connect the crank member 226 to the connector link 240 cause the first end 241 of the connector link 240 to also rotate in a circular path around the shaft 224 of the motor 222. As the first end 241 of the connector link 240 rotates, the tamper member 220 reciprocates downward in the vertical direction toward the first surface 107 of the second substrate 106 and the set of guide links 232 pivot. The guide links 232 limit the movement of the tamper member 220 to a defined trajectory, T, as the tamper member 220 moves toward the drum 112. The tamper member 220 contacts the first surface 107 of the second substrate 106 as the shaft 224 of the motor 222 approaches the second angular position 266, causing the second substrate 106 to be pressed against the first surface 109 of the discrete component 102 on the outer circumferential surface 124 of the drum 112. The tamper apparatus 136 is in the second configuration 286 when the tamper member 220 presses the second substrate 106 against the discrete component 102 on the outer circumferential surface 124 of the drum 112. The adhesive 113 on the first surface 109 of the discrete component 102 acts to adhere the second surface 108 of the second substrate 106 to the first surface 109 of the discrete component 102. To complete one revolution, the tamper apparatus 136 shifts from the second configuration 286 back to the first configuration 284. The shaft 224 of the motor 222 continues rotating from the second angular position 266 back to the first angular position 264 and the crank member 226 rotates from a second position 282 to a first position 280. The tamper apparatus 136 continuously rotates back and forth from the first configuration 284 to the second configuration 286 through multiple revolutions in order to join subsequent discrete components to the second substrate 106.

With reference to FIGS. 2A and 3A, the tamper member 220 may be configured to displace the target area 115 of the second surface 108 of the second substrate 106 into contact with the first surface 109 of the discrete component 102. In particular, the tamper member 220 may displace the first surface 107 of the second substrate 106 and press the target area 115 of the second surface 108 of the second substrate 106 against the first surface 109 of the discrete component 102 on the outer circumferential surface 124 of the drum 112.

Figure 7:
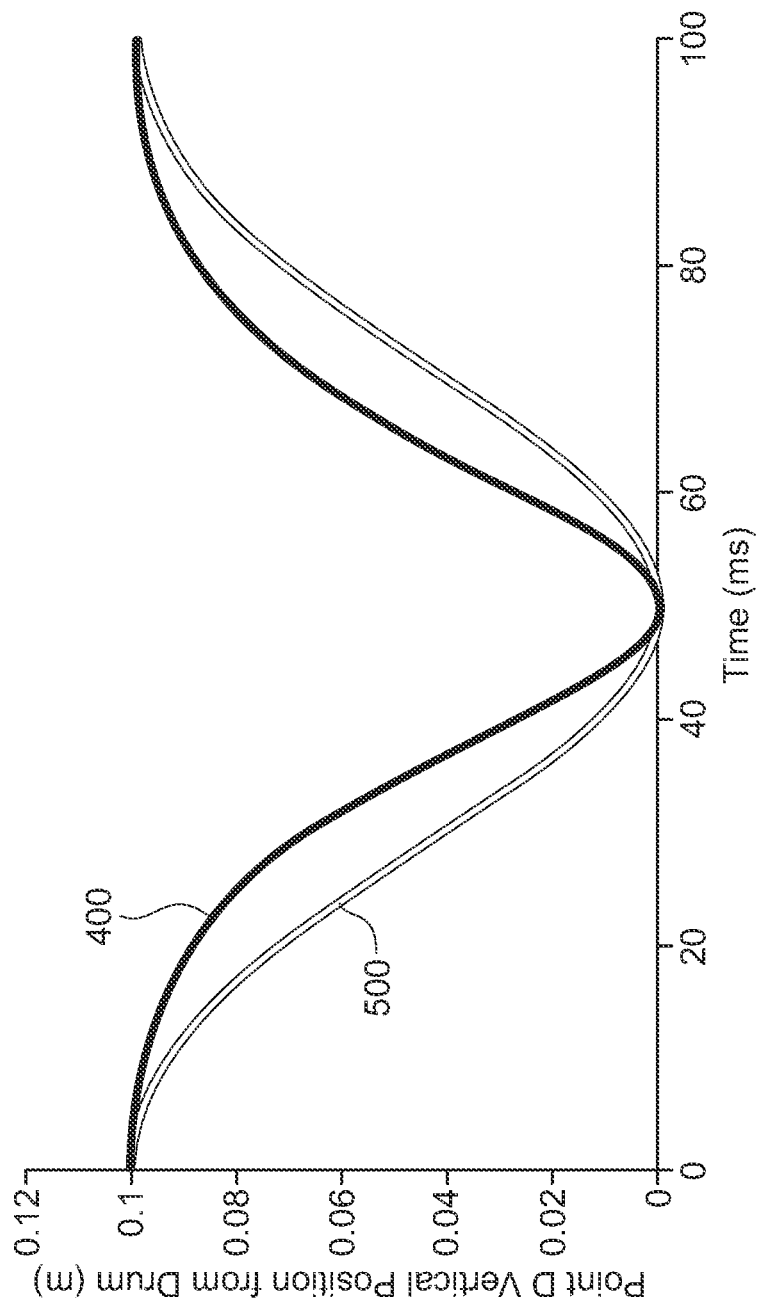
FIG. 7 is a plot of the vertical position of point D from the outer circumferential surface of the drum with the motor operating at a variable angular velocity over one revolution overlaid with a plot of the vertical position of point D from the outer circumferential surface of the drum with a motor operating at a constant angular velocity over one revolution.

The shaft of the motor is configured to continuously rotate at a variable angular velocity, causing the velocity of the tamper member in the vertical direction, Y, to change during each revolution. FIG. 7 shows a graph 400 of the vertical position of point D from the outer circumferential surface of the drum with the motor operating at a variable angular velocity over one revolution. FIG. 7 also includes graph 500 of the vertical position of point D from the outer circumferential surface of the drum with a motor operating at a constant angular velocity over one revolution. With regard to graphs 400 and 500, the tamper member compresses against the drum at zero meters. Time is represented on the x-axis. As shown in FIG. 7, for each revolution, the tamper member is relatively near the outer circumferential surface of the drum for a shorter period of time when the motor is operating at a variable angular velocity compared to a motor operating at a constant angular velocity. A motor configured to rotate the shaft at a variable angular velocity can speed up and slow down through one revolution in order to limit the time the tamper member directs the second substrate toward the outer circumferential surface of the drum. Whereas, when the motor is programmed to drive the shaft of the motor with a constant angular velocity, the motor must drive the shaft at a higher constant angular velocity in order to limit the time the motor is contacting the outer circumferential surface of the drum. However, speeding up a motor operating at a constant angular velocity decreases the total time of one revolution. In some exemplary configurations, the total time for one revolution may be preselected based upon the spacing requirements of the discrete components on the second substrate. In that case, operating the motor at a variable angular velocity may limit the time the tamper member contacts the second substrate while also maintaining the preselected amount of time between attachment of adjacent discrete components.

Figure 8:
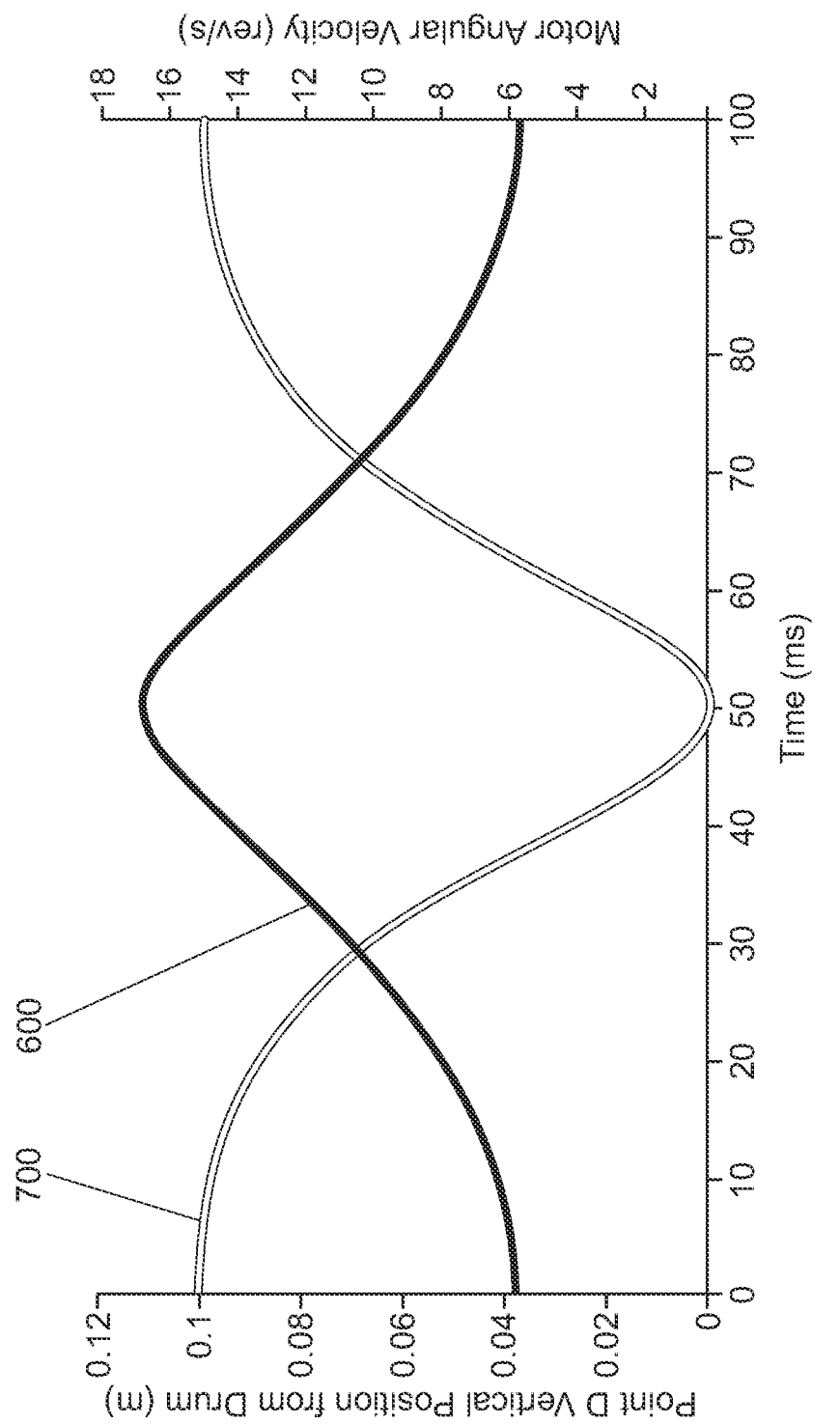
FIG. 8 is a plot of the vertical position of point D from the outer circumferential surface of the drum with the motor operating at a variable angular velocity over one revolution overlaid with a plot of the angular velocity of the shaft of the motor over one revolution.

FIG. 8 shows a graph 600 of the vertical position of point D from the outer circumferential surface of the drum with the motor operating at a variable angular velocity over one revolution. FIG. 8 also shows a graph 700 of the angular velocity of the shaft of the motor over one revolution. Time is represented on the x-axis. As shown in FIG. 8, as the tamper member approaches the outer circumferential surface of the drum at zero meters, the angular velocity of the shaft of the motor is increasing. Once the tamper member is in the second position, the angular velocity is at the highest angular velocity for each revolution. The angular velocity of the shaft of the motor then decreases as the tamper member shifts away from the outer circumferential surface of the drum. The angular velocity of the motor is at lowest angular velocity when the tamper member is furthest from the drum at the first position.

Figure 9:
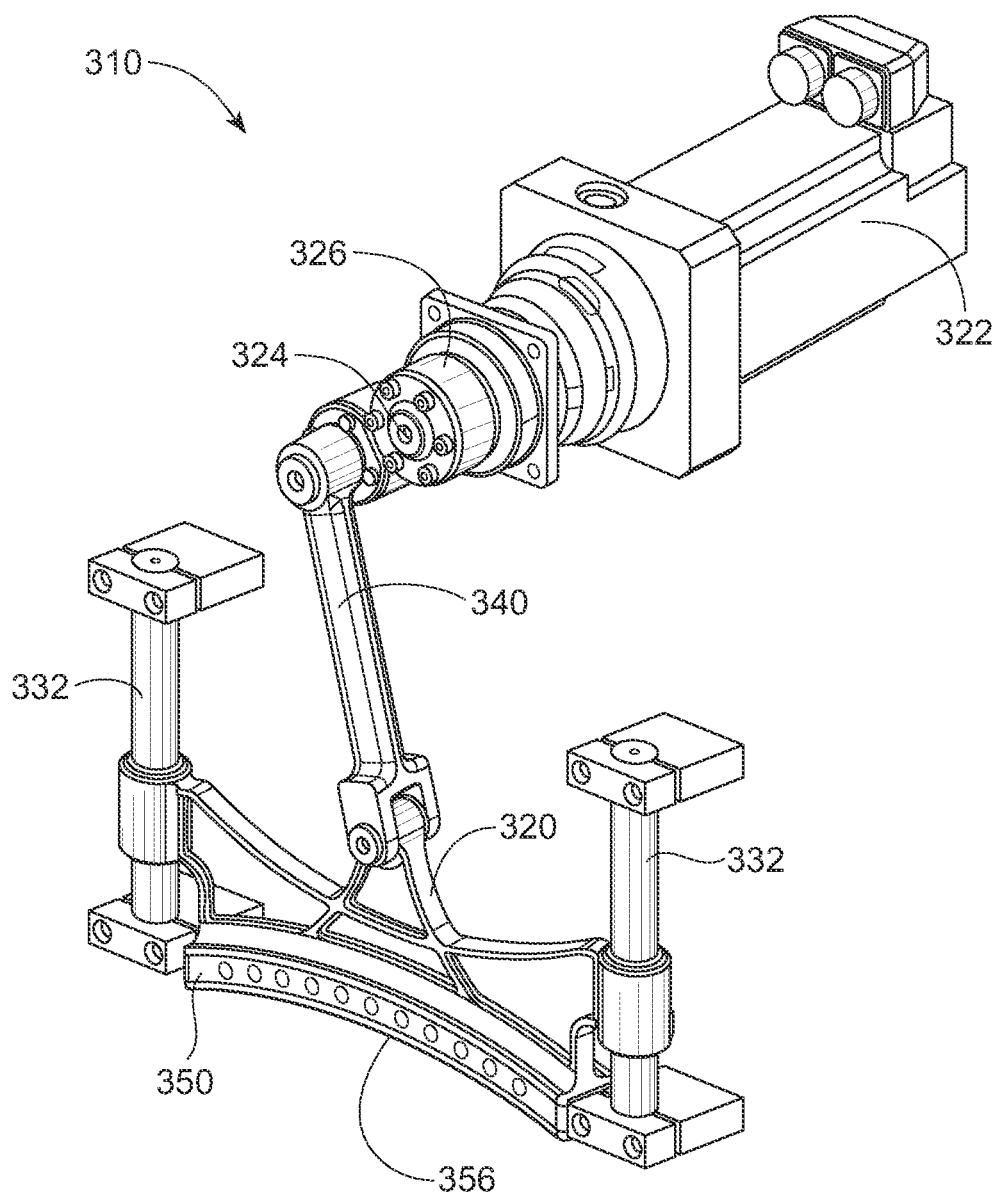
FIG. 9 is a perspective side view of a tamper apparatus.

FIG. 9 shows a perspective side view of an embodiment of a tamper apparatus. As shown in FIG. 9, the tamper apparatus 326 may include a servo motor 322 having a shaft 324. The shaft of the motor 322 is operatively connected to a crank member 326 at one end of the crank member 326. The opposite end of the crank member 326 is rotatably connected to a connector link 340. The connector link 340 is also rotatably connected to a tamper member 320. The tamper member 320 may be connected with two guide bars 332 in order to limit the trajectory of a point on the tamper member 320 to a straight line. The tamper member 320 may also include a compressible member 350 having a skin 356.

With reference to FIG. 1, the conveyor apparatus 202 may be in the form of a localized speed varying apparatus 203 that may slow or stop the second substrate 106 in the machine direction MD. As the second substrate 106 is stopped or slowed, the tamper apparatus 136 is able to more precisely join the discrete component 102 to the second substrate 106. While the second substrate 106 is temporarily stopped in the machine direction MD, the drum 112 continues to rotates in the cross direction CD while the tamper apparatus 136 contacts the second substrate 106 and discrete component 102 against the outer circumferential surface 124 of the drum 112. It is to be appreciated that the compressible member 250 may deform while the tamper apparatus 136 compresses the second substrate 106 against the discrete component 102 on the outer circumferential surface 124 of the drum 112. As a result, the discrete component 102 may remain in the same cross-directional position relative to the second substrate 106 even though the drum 112 continues rotating in the cross direction CD.

Figure 10:
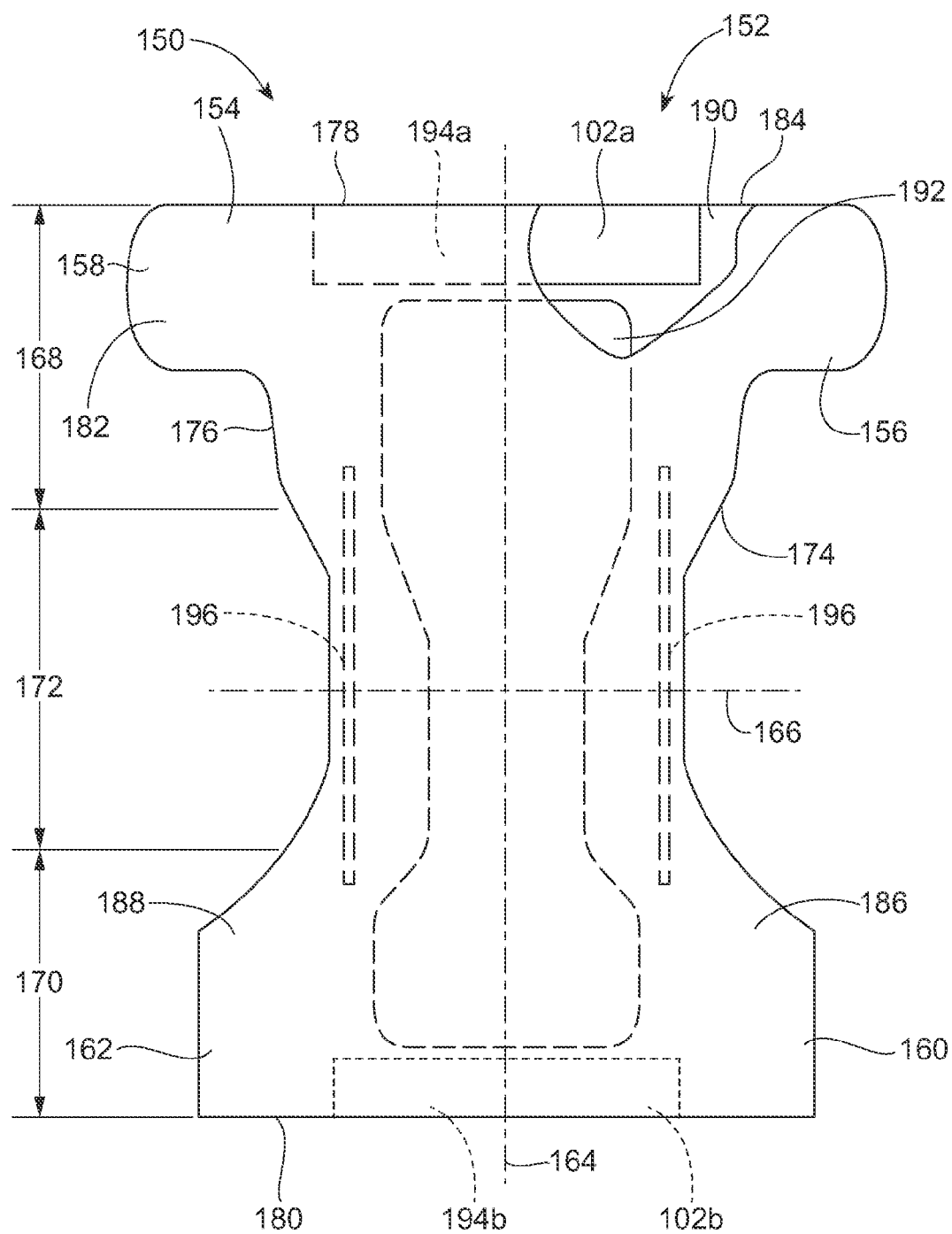
FIG. 10 is a plan view of a disposable absorbent article having a discrete waistband and is partially cut away to show the construction of and various features that may be included in a disposable absorbent article.

A number of different products may be manufactured in accordance with the methods described herein. For the purposes of a specific illustration, FIG. 10 shows one example of a disposable absorbent article 150 in the form of a diaper 152 that may include a discrete component 102 attached thereto in accordance with the present disclosure. In particular, FIG. 10 is a plan view of one embodiment of a diaper 152 including a chassis 154 shown in a flat, unfolded condition, with the portion of the diaper 152 that faces a wearer oriented towards the viewer. A portion of the chassis structure is cut-away in FIG. 10 to more clearly show the construction of and various features that may be included in exemplary configurations of the diaper.

As shown in FIG. 10, the diaper 152 includes a chassis 154 having a first ear 156, a second ear 158, a third ear 160, and a fourth ear 162. As discussed above, while the present disclosure discusses joining discrete components in the form of waistbands to absorbent articles, it is to be appreciated that the tamper apparatus may be used to join other discrete components such as ears 156, 158, 160, and 162, for example, to absorbent articles. To provide a frame of reference for the present discussion, the chassis is shown with a longitudinal axis 164 and a lateral axis 166. The chassis 154 is shown as having a first waist region 168, a second waist region 170, and a crotch region 172 disposed intermediate the first and second waist regions. The periphery of the diaper is defined by a pair of longitudinally extending side edges 174, 176; a first outer edge 178 extending laterally adjacent the first waist region 168; and a second outer edge 180 extending laterally adjacent the second waist region 170. As shown in FIG. 10, the chassis 154 includes an inner, body-facing surface 182, and an outer, garment-facing surface 184.

As shown in FIG. 10, the chassis 154 of the diaper 152 may include an outer covering layer 186 including a topsheet 188 and a backsheet 190. An absorbent core 192 may be disposed between a portion of the topsheet 188 and the backsheet 190. As discussed in more detail below, one or more of the regions may be stretchable and may include an elastomeric material or layered elastic substrate as described herein. As such, the diaper 152 may be configured to adapt to a specific wearer's anatomy upon application and to maintain coordination with the wearer's anatomy during wear.

Although the first and second ears 156, 158 as well as the third and fourth ears 160, 162 shown in FIG. 10 are illustrated as being integrally formed with the chassis 154, it is to be appreciated that other embodiments may include ears that are discrete elements connected with the chassis. In some embodiments, the ears are configured to be stretchable. The ears may also include one or more fastener elements adapted to releasably connect with each other and/or other fastener elements on the chassis. A more detailed discussion of stretchable ears can be found in U.S. Pat. Nos. 4,857,067; 5,151,092; 5,674,216; 6,677,258; 4,381,781; 5,580,411; and 6,004,306. The ears may also include various geometries and arrangements of stretch zones or elements, such as discussed in U.S. Pat. Publication Nos. US 2005/0215972A1 and US 2005/0215973A1.

As shown in FIG. 10, the diaper 152 may include leg cuffs 196 that may provide improved containment of liquids and other body exudates. The leg cuffs 196 may be disposed in various ways on the diaper 152. For example, the leg cuffs 196 may be disposed on the outer, garment-facing surface 184 of the chassis 154; the inner, body-facing surface 182; or between the inner and outer facing surfaces 182 or 184. Leg cuffs 196 may also be referred to as leg bands, side flaps, barrier cuffs, or elastic cuffs. U.S. Pat. No. 3,860,003 describes a disposable diaper that provides a contractible leg opening having a side flap and one or more elastic members to provide an elasticized leg cuff (a gasketing cuff). U.S. Pat. Nos. 4,808,178 and 4,909,803 describe disposable diapers having "stand-up" elasticized flaps (barrier cuffs). U.S. Pat. Nos. 4,695,278 and 4,795,454 describe disposable diapers having dual cuffs, including gasketing cuffs and barrier cuffs.

The diaper may be provided in the form of a pant-type diaper or may alternatively be provided with a re-closable fastening system, which may include fastener elements in various locations to help secure the diaper in position on the wearer. For example, fastener elements may be located on the first and second ears and may be adapted to releasably connect with one or more corresponding fastening elements located in the second waist region. It is to be appreciated that various types of fastening elements may be used with the diaper. In one example, the fastening elements include hook & loop fasteners, such as those available from 3M or Velcro Industries. In other examples, the fastening elements include adhesives and/or tap tabs, while others are configured as a macrofastener or hook (e.g., a MACRO or "button-like" fastener). Some exemplary fastening elements and systems are disclosed in U.S. Pat. Nos. 3,848,594; 4,662,875; 4,846,815; 4,894,060; 4,946,527; 5,151,092; and 5,221,274. Additional examples of fasteners and/or fastening elements are discussed in U.S. Pat. Nos. 6,251,097 and 6,432,098; and U.S. Patent Publication Nos. 2007/0078427 and 2007/0093769. Other fastening systems are described in more detail in U.S. Pat. Nos. 5,595,567; 5,624,427; 5,735,840; and 5,928,212. The fastening system may also provide a means for holding the article in a disposal configuration as disclosed in U.S. Pat. No. 4,963,140.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird, et al published on Sep. 20, 2007, US 2011/0139658A1 Hird, et al published on Jun. 16, 2011, US 2011/0139657A1 Hird et al published on Jun. 16, 2011, US 2011/0152812A1 Hird et al published on Jun. 23, 2011, US 2011/0139662A1 Hird, et al published on Jun. 16, 2011, and US 2011/0139659A1 Hird, et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

The absorbent article may also include discrete components 102a and 102b such as shown in FIG. 10 in the form of first and second waistbands 194a and 194b. The first and second waistbands 194a and 194b may provide improved fit and waste containment. The first and second waistbands 194a and 194b may be located in the first waist region 168 and/or the second waist region 170. The first and second waistbands 194a and 194b may be configured to elastically expand and contract to dynamically fit the wearer's waist.

The first and second waistbands 194a and 194b can be incorporated into the diaper in accordance with the methods discussed herein and may extend at least longitudinally outwardly from the absorbent core 192 and generally form at least a portion of the first and/or second outer edges 178, 180 of the diaper 152. In addition, the first and second waistbands 194a and 194b may extend laterally to include the ears. While the first and second waistbands 194a and 194b or any constituent elements thereof may comprise one or more separate elements affixed to the diaper, the first and second waistbands 194a and 194b may be constructed as an extension of other elements of the diaper, such as the backsheet 190, the topsheet 188, or both the backsheet 190 and the topsheet 188. In addition, the first and second waistbands 194a and 194b may be disposed on the outer, garment-facing surface 184 of the chassis 154; the inner, body-facing surface 182; or between the inner and outer facing surfaces. It is to be appreciated that the first and second waistbands 194a and 194b shown in FIG. 10 may comprise the same materials and/or may have the same structure. While in other exemplary configurations, the first and second waistbands 194a and 194b may comprise different materials and/or may have different structures. The first and second waistbands 194a and 194b may be constructed in a number of different configurations including those described in U.S. patent application Ser. No. 61/499, 294; and U.S. Patent Publication Nos. 2007/0142806; 2007/0142798; and 2007/0287983.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for applying a discrete component from a first substrate to a second substrate, the apparatus comprising:
    a drum having an outer circumferential surface;
    a cutter positioned to cut the first substrate on the outer circumferential surface of the drum into a plurality of discrete components;
    a conveyor for positioning the second substrate proximate to, but not in contact with, the outer circumferential surface of the drum;
    a programmable servo motor having a shaft, wherein the shaft continuously rotates at a variable angular velocity in a single direction, wherein the servo motor is configured to rotate the shaft in a first phase and a second phase, wherein the shaft is constrained to rotate from a first angular position to a second angular position in a first time in the first phase, and wherein the shaft is constrained to rotate from the second angular position to the first angular position in a second time in the second phase; and
    a tamper member associated with the shaft of the servo motor, wherein when the shaft rotates in the first phase, the tamper member travels from a first position to a second position to displace a selected portion of the second substrate into contact with the discrete component on the outer circumferential surface of the drum.

2. The apparatus of claim 1 further comprising:
    a crank member connected with the shaft; and
    a connector link connected with the crank member, wherein the tamper member is connected to the connector link, and wherein the cutter comprises a knife roll.

3. The apparatus of claim 1, wherein when the shaft rotates in the second phase, the tamper member travels from the second position to the first position to move the tamper member away from the second substrate and the drum.

4. The apparatus of claim 1, wherein the angular velocity of the shaft of the motor increases in the first phase.

5. The apparatus of claim 1, wherein the angular velocity of the shaft of the motor decreases in the second phase.

6. The apparatus of claim 1 further comprising a guide link operatively connected to the tamper member to limit movement of the tamper member to a defined trajectory.

7. The apparatus of claim 1, wherein the conveyor comprises a localized speed varying apparatus.

8. The apparatus of claim 1 further comprising a compressible member operatively connected with a bottom surface of the tamper member.

9. The apparatus of claim 8, wherein the compressible member comprises a urethane skin.

10. The apparatus of claim 1, wherein the tamper member has a bottom surface, wherein the outer circumferential surface of the drum has a contour, and wherein the bottom surface of the tamper member is contoured to match the contour of the outer circumferential surface of the drum.

11. The apparatus of claim 1, wherein the drum comprises a plurality of vacuum openings on the outer circumferential surface thereof for applying vacuum force to releasably hold the discrete component on the outer circumferential surface of the drum.

12. An apparatus for applying discrete components of a first substrate to target areas of a second substrate, the apparatus comprising:
    a programmable servo motor having a shaft, wherein the shaft continuously rotates at a variable angular velocity in a single direction, wherein the servo motor is programmed to rotate the shaft in a first phase and a second phase, wherein the shaft is constrained to rotate from a first angular position to a second angular position in a first time in the first phase, and wherein the shaft is constrained to rotate from the second angular position to the first angular position in a second time in the second phase;
    a crank member connected with the shaft;
    a connector link connected with the crank member; and
    a tamper member connected with the connector link, the tamper member positioned proximate to the second substrate in line with a discrete component of the first substrate, wherein when the shaft rotates in the first phase, the tamper member travels from a first position to a second position to displace the target area of the second substrate into contact with the discrete component.

13. The apparatus of claim 12, further comprising:
    a drum positioned proximate to the tamper member for advancing the first substrate;
    a knife roll positioned to cut the first substrate into a plurality of discrete components on the drum; and
    a conveyor for positioning the second substrate proximate to, but not in contact with, the drum.

14. The apparatus of claim 12, wherein the angular velocity of the shaft of the motor increases in the first phase.

15. The apparatus of claim 12, wherein the angular velocity of the shaft of the motor decreases in the second phase.

* * * * *